United States Patent [19]

Folkers et al.

[11] Patent Number: 4,504,414

[45] Date of Patent: Mar. 12, 1985

[54] SYNTHETIC PYRIDYL-ALANYL DECAPEPTIDES HAVING ANTIOVULATORY ACTIVITY

[75] Inventors: Karl Folkers, Austin, Tex.; Cyril Y. Bowers, New Orleans, La.; Teresa M. Kubiak, New York, N.Y.; Janusz Stepinski, Austin, Tex.

[73] Assignee: Board of Regents, The University of Texas System, Austin, Tex.

[21] Appl. No.: 479,645

[22] Filed: Mar. 28, 1983

[51] Int. Cl.$^3$ ............................................. C07C 103/52
[52] U.S. Cl. ..................... 260/112.5 LH; 260/112.5 R
[58] Field of Search ............... 260/112.5 LH, 112.5 R

[56] References Cited

U.S. PATENT DOCUMENTS 3,655,636 4/1972 Young ........................... 260/112.5 R
4,310,517 1/1982 Etschenberg et al. ....... 260/112.5 R

OTHER PUBLICATIONS

Humphries et al., *J. of Med. Chem.*, 22, No. 7, 774–777 (1979).
Nestor et al., *J. Med. Chem.*, 25, No. 7, 795–801 (1982).
Coy et al., *Endocrinology*, 110, No. 4, 1445–1447 (1982).
Nekola et al., *Science*, 218, 160–162 (1982).
Katzorke et al., *Fertility and Sterility*, vol. 36, 1981, p. 388, Contraceptive Effects of an Agonistic LH-RH Analog.
Asch, *Fertility and Sterility*, vol. 36, 1981, p. 388, Antiovulatory Activity of a Potent LH-RH Antagonistic Analogue (N–Ac–D–Trp$^{1,3}$, D–p–Cl–Phe$^2$, D–Phe$^6$, D–Ala$^{10}$) LH–RH (A–LH–RH).

*Primary Examiner*—Delbert R. Phillips
*Assistant Examiner*—F. T. Moezie
*Attorney, Agent, or Firm*—Arnold, White & Durkee

[57] ABSTRACT

Pyridyl-alanyl decapeptides have been effectively synthesized and found to have antiovulatory activity. The exemplary [N-Ac-D-2-Nal$^1$,pCl-D-Phe$^2$, D-3-Pal$^3$,D-Arg$^6$,D-Ala$^{10}$]-LHRH has very high potency to inhibit ovulation, both parenterally and orally. Also, this exemplary pyridyl-alanyl-decapeptide showed an unexpected prolonged duration of antiovulatory activity. Such pyridyl-alanyl-decapeptides are useful to control reproduction.

10 Claims, No Drawings 4,504,414

SYNTHETIC PYRIDYL-ALANYL DECAPEPTIDES HAVING ANTIOVULATORY ACTIVITY

BACKGROUND OF THE INVENTION

During the decade, over a thousand analogs of the luteinizing hormone releasing hormone (LHRH) have been internationally synthesized, some of which were significant agonists, "super-agonists" or antagonists. The biological goal of antagonists of LHRH is effective and potent antiovulatory activity toward control of conception. Folkers, Humphries and Bowers [Z. Naturforsch. 37b, 246–249 (1982)] critiqued the evolution of design and achievement of inhibitors of LHRH as inhibitors of ovulation, based on the research of many investigators. A recent significant advance in sequence changes to increase antiovulatory potency was reported by Coy et al. [Endocrinology 110, 1445–1447 (1982)] on the—"unexpectedly favorable outcome"—of introducing D-Lys and D-Arg in position 6. D-Arg[6] was superior to D-Lys[6] in a pair, and [N-Ac-pCl-D-Phe[1,2],D-Trp[3],D-Arg[6],D-Ala[10]]-LHRH caused 100% inhibition of ovulation at 1.5 μg and 40% at 0.75 μg.

Nestor et al. [J. Med. Chem. 25, 795–801 (1982)] synthesized and bioassayed several very hydrophobic analogs of LHRH for super-agonistic activity. They found that β-(2-naphthyl)-D-α-alanine, when introduced into position 6 of LHRH, resulted in one of the most potent LHRH agonists ever reported. Such an agonist was comparable to or more potent than the widely studied LHRH agonist having D-Trp[6].

Although a diversity of agonists and antagonists related to LHRH, which have D-tryptophan in position 3 and/or 6, have been far greater investigated than analogs having a naphthyl-alanine, the bicyclic nature of the indole and naphthalene nucleus with and without a nitrogen atom, was a basis for our initiation of the synthesis of several heterocyclic analogs of tryptophan and naphthylalanine, in the D-configuration, and the insertion of these heterocyclic amino acids into analogs of LHRH. Initially, analogs containing quinolylalanines and pyridylalanines were synthesized, because these amino acids combine basicity, aromaticity and hydrophilicity in the same molecule. We report the results of the synthesis and bioassay of analogs of LHRH containing pyridyl-alanyl moieties.

THE INVENTION

It has been discovered, in accordance with the present invention, that decapeptides containing moieties of pyridylalanines, which are synthesized by the automatic solid-phase method, have exceptionally potent activity to inhibit ovulation both parenterally and orally and quite unexpectedly to show a long duration of antiovulatory activity, in vivo. Deprotection and cleavage of the decapeptide from the resin is accomplished by hydrogen fluoride and the resulting peptidic material is purified to yield the pure decapeptides containing moieties of pyridylalanines.

In accordance with the present invention, several exemplary decapeptides containing moieties of pyridylalanines were synthesized as follows.

EXAMPLES

Benzhydrylamine (BHA) resin hydrochloride and the amino acid intermediates were purchased from Peninsula Labs., San Carlos, Calif. The α-amino functions were protected by the BOC-group, except for L-arginine which had the AOC-group. The functional groups for side chains were protected by the benzyl group for serine, the tosyl group for arginine and the o-bromocarbobenzoxy group for tyrosine. D-α-amino-n-butyric acid was purchased from the Sigma Chemical Co., St. Louis, Mo. BOC-p-Chloro-D-phenylalanine, β-(2-pyridyl)-D-α-alanine, β-(4-pyridyl)-D-α-alanine, BOC-β-(2-naphthyl)-D-α-alanine and BOC-3,4-dichloro-D-phenylalanine were provided by the Southwest Foundation for Research and Education, San Antonio, Tex., through courtesy of Dr. Marvin Karten, Center for Population Research, National Institutes of Health, Bethesda, Md. β-(3-Pyridyl)-D-α-alanine dihydrochloride was synthesized [K. Folkers et al., unpublished data]. The optical rotations were measured in a Perkin-Elmer 141 polarimeter with a digital readout.

BOC-β-(2-Pyridyl)-D-α-alanine;
BOC-β-(3-Pyridyl)-D-α-alanine;
BOC-β-(4-Pyridyl)-D-α-alanine These three BOC derivatives were prepared essentially by the general procedure of Moroder et al. [Hoppe-Seyler's Z. Physiol. Chem. 357, 1651 (1976)].

After recrystallization from chloroform-ethyl acetate-heptane, the properties of BOC-β-(2-Pyridyl)-D-α-alanine were: m.p. 149°–150° C. $[\alpha]_D = +15.2$ (c 1.0, methanol), $[\alpha]_D = +35.6$ (c 1.00, DMF). BOC-β-(2-pyridyl)-L-α-alanine was reported [K. Hsieh, E. C. Jorgensen and T. C. Lee; J. Med. Chem. 22, 1199 (1979)] to melt at 146°–146.5° C. After crystallization from ethyl acetate/heptane, the properties of BOC-β-(3-pyridyl)-D-α-alanine were: m.p. 138°–139° C. $[\alpha]_D = -7.1$ (c 1.0, methanol) and $[\alpha]_D = -17.4$ (c 1.07, 95% ethanol). After crystallization from methanol, the properties of BOC-β-(4-pyridyl)-D-α-alanine were: m.p. 233° C., dec., $[\alpha]_D = +30.6°$ (c 1.0, DMF).

Peptide Synthesis. The peptides were synthesized by the solid-phase method using a Beckman Model 990 Peptide Synthesizer. The attachment of the first amino acid to the benzhydrylamine resin, elongation of the peptide chain, acetylation of the N-terminus and HF cleavage were as described [K. Folkers, C. Y. Bowers, F. Momany, K. J. Friebel, T. Kubiak and J. Maher; Z. Naturforsch. 37b, 872–876 (1982)]. BOC-β-(2-Pyridyl)-D-α-alanine was inserted into the peptide III (Table 1) by the EEDQ method [H. Yajima and H. Kawatani; Chem. Pharm. Bull. 19, 1905 (1971)]. The steps of purification of each peptide are indicated in Table 2. The purification of these crude peptides was achieved by an appropriate choice of steps from among the following steps: (A) gel filtration over Sephadex G-25 with 20% acetic acid; (B) chromatography over silica gel 60 (230–400 mesh) with n-butanol-acetic acid-water, 4:1:5, upper phase; (C) semi-preparative high pressure liquid chromatography on a μ-Bondapak C[18] column in linear gradients of buffer A (0.05M ammonium acetate, pH 5.0) and buffer B (20% buffer A+80% acetonitrile). The purity of the peptides was evidenced by single spots on silica gel TLC (Merck) plates using the following solvent systems: n-butanol-acetic acid-ethyl acetate-water, 1:1:3:1; n-butanol-acetic acid-water, 4:1:5 upper phase; n-butanol-pyridine-acetic acid-water, 15:10:3:12; ethyl acetate-pyridine-acetic acid-water, 20:5:2:3. The spots were detected by a UV-lamp and the chlorine/o-tolidine reagent. HPLC was the ultimate criterion for purity of the peptides. Equipment of Waters Associates, Milford, Mass., with a gradient programmer and μ-Bondapak $C_{18}$ reversed phase column (30 cm) were used. The solvent systems were: buffer A: 0.01M $KH_2PO_4$, pH 3.0; buffer B: 50% buffer A/50% acetonitrile (v/v). The linear gradient was 40–100% of B in 20 minutes, flow rate, 2.0 ml/min.; monitored at 210 nm. The retention times of the peptides on HPLC are in Table 2. The amino acid analyses were carried out on a Beckman 118 CL automatic amino acid analyzer equipped with a Hewlett Packard 3390A Integrator. The hydrolysis of the peptides was in constant boiling HCl with phenol. The amino acid compositions are in Table 2.

Biological Assays. The peptides were assayed for activity to inhibit ovulation in rats, as described [J. Humphries, Y.-P. Wan, K. Folkers and C. Y. Bowers; J. Med. Chem. 21, 120–123 (1978)]. The procedure for assay when the antagonist is administered orally is the same except for the route of administration.

The analogs of LHRH were synthesized by the solid-phase procedure using the DCC-HOBt coupling method for the BOC-amino acids, but with one exception, BOC-$\beta$-(2-pyridyl)-D-$\alpha$-alanine was inserted into analog III by the EEDQ (1-ethoxy-carbonyl-2-ethoxy-1,2-dihydro-quinoline) method [H. Yajima and H. Kawatani; Chem. Pharm. Bull. 19, 1905 (1971)]. When the DCC-HOBt coupling method was used with BOC-$\beta$-(2-pyridyl)-D-$\alpha$-alanine, an immediate and intense dark brown coloration appeared. Hsieh et al. [J. Med. Chem. 22, 1199 (1979)] reported a comparable coloration with racemization. The steps of purification, and HPLC data on purity are in Table 2.

The presence of D-tryptophan in positions 3 and 6 of a diversity of antagonists of LHRH as studied by many investigators has been a prominent sequence feature of antagonists. One of the purposes of this study was to synthesize and insert several heterocyclic analogs of tryptophan, generally in the D-configuration. Quinolylalanines [M. V. Nekola, A. Horvath, J.-J. Ce, C. H. Coy and A. V. Schally; Science 218, 160–162 (1982)] and pyridylalanines were initially synthesized and introduced into analogs of LHRH. The analogs in Table 1 represent the three pyridyl analogs, namely, $\beta$-(2-pyridyl)-, $\beta$-(3-pyridyl)- and $\beta$-(4-pyridyl)-D-$\alpha$-alanine. As for D-tryptophan in positions 3 and/or 6, these three pyridylalanines were substituted generally in positions 3 and/or 6.

When these pyridylalanines became synthetically available as BOC-intermediates, they were inserted into analogs based upon [Ac-(pCl-D-Phe)[1,2], D-Trp[3],D-Arg[6],D-Ala[10]]-LHRH, which was then known as the most potent antagonist. This antagonist of Coy et al. [Endocrinology 110, 1445–1447 (1982)] constituted an

TABLE 1

Antiovulatory Activities of LHRH Antagonists

| No. | LHRH Analog | Dose (μg) | % AOA[b] | Rats ovu. No. rats |
|---|---|---|---|---|
| I. | [N—Ac—(pCl—D-Phe)[1,2],D-Trp[3],D-Arg[6],D-Ala[10]]—LHRH | 0.75 | 40 | 6/10[a] |
|  |  | 1.0 | 83 | 1/6 |
|  |  | 1.5 | 100 | 0/10[a] |
| II. | [N—Ac—(pCl—D-Phe)[1,2],D-3-Pal[3],D-Arg[6],D-Ala[10]]—LHRH | 0.5 | 58 | 8/19 |
|  |  | 1.0 | 78 | 3/14 |
| III. | [N—Ac—(pCl—D-Phe)[1,2],D-2-Pal[3],D-Arg[6],D-Ala[10]]—LHRH | 1.0 | 29 | 5/7 |
| IV. | [N—Ac—(pCl—D-Phe)[1,2],D-4-Pal[3],D-Arg[6],D-Ala[10]]—LHRH | 0.5 | 14 | 6/7 |
|  |  | 6.0 | 33 | 6/9 |
| V. | [N—Ac—(pCl—D-Phe)[1,2],D-3-Pal[3,6],D-Ala[10]]—LHRH | 1.0 | 50 | 5/10 |
|  |  | 3.0 | 100 | 0/7 |
| VI. | [N—Ac—(pCl—D-Phe)[1,2],D-4-Pal[3,6],D-Ala[10]]—LHRH | 6.0 | 62.5 | 3/8 |
| VII. | [N—Ac—(pCl—D-Phe)[1,2],D-Trp[3],D-3-Pal[6],D-Ala[10]]—LHRH | 2.0 | 13 |  |
| VIII. | [N—Ac—(pCl—D-Phe)[1,2],D-3-Pal[3],D-Trp[6],D-Ala[10]]—LHRH | 1.0 | 0 | 10/10 |
| IX. | [N—Ac—(pCl—D-Phe)[1,2],D-3-Pal[3],D-Arg[6],D-Abu[10]]—LHRH | 1.0 | 10 | 9/10 |
| X. | [N—Ac—(pCl—D-Phe)[1,2],D-3-Pal[3,6]]—LHRH | 1.0 | 17 | 5/6 |
|  |  | 3.0 | 86 | 1/7 |
| XI. | [N—Ac—D-2-Nal[1],pCl—D-Phe[2],D-3-Pal[3],D-Arg[6], D-Ala[10]]—LHRH | 0.5 | 100 | 0/9 |
|  |  | 0.25 | 57 | 3/7 |
| XII. | [N—Ac—3,4-diCl—D-Phe[1],pCl—D-Phehu 2,D-3-Pal[3],D-Arg[7], D-Ala[10]]—LHRH | 0.5 | 82 | 9/11 |
|  |  | 0.25 | 0 | 9/9 |

[a]D. H. Coy, A. Horvath, M. V. Nekola, E. J. Coy, J. Erchegyi and A. V. Schally; Endocrinology 110, 1445–1447 (1982).
[b]% inhibition of ovulation in rats

TABLE 2

Characterization of LHRH Analogs

| No. | Purification method(s) | HPLC Data | | Amino Acid Composition* | | | | | |
|---|---|---|---|---|---|---|---|---|---|
|  |  | Purity (%) | R.T. (min.)+ | Ser | Pro | Ala Gly** | Leu | Tyr | Arg |
| II | B | 99 | 9.0 | 0.94 | 1.03 | 1.04 | 1.00 | 1.01 | 1.97 |
| III | B | 97 | 10.7 | 0.83 | 1.02 | 1.02 | 1.08 | 1.01 | 2.05 |
| IV | C | 97 | 8.6 | 0.96 | 0.96 | 1.10 | 0.97 | 1.00 | 2.03 |
| V | B | 99 | 10.2 | 0.95 | 1.03 | 1.04 | 1.01 | 0.99 | 0.99 |
| VI | A,C | 98 | 9.1 | 0.92 | 0.96 | 1.08 | 1.00 | 1.02 | 1.01 |
| VII | C | 97 | 15.2 | 0.89 | 0.99 | 1.05 | 1.01 | 0.97 | 1.07 |
| VIII | B | 98 | 15.2 | 0.87 | 1.11 | 1.05 | 1.00 | 0.97 | 1.02 |
| IX | B | 98 | 9.5 | 0.91 | 1.05 | — | 1.02 | 1.02 | 2.02 |
| X | A,C | 98 | 10.4 | 0.94 | 1.01 | 1.04** | 1.00 | 0.99 | 1.03 |
| XI | B | 98 | 9.6 | 0.95 | 0.97 | 1.02 | 1.04 | 1.03 | 2.03 |
| XII | B,C | 99 | 10.4 | 0.97 | 0.97 | 1.05 | 1.05 | 1.01 | 1.96 |

*Trp, Abu, 2-Pal, 3-Pal, pClPhe, 2-Nal and 3,4-diClPhe were detected but not quantitated.
+0.01 M $KH_2PO_4$, pH 3.0. For details see EXAMPLES

CHEMICAL RESULTS AND BIOLOGICAL ACTIVITIES advance in potency based on the observation that D-Lys$^6$ or better, D-Arg$^6$ significantly increased activity of an antagonist. Therefore, some but not all analogs having a pyridylalanine moiety were based on this peptide as a model.

having other substituents in position 1, particularly including the non-aromatic amino acids.

|  |  | Dose (μg) | % AOA | Rats ovu. No. rats |
|---|---|---|---|---|
| XI. | [N—Ac—D-2-Nal$^1$,pCl—D-Phe$^2$,D-3-Pal$^3$,D-Arg$^6$,D-Ala$^{10}$]—LHRH | 0.5 | 100 | 0/9 |
| XII. | [N—Ac—3,4-diCl—D-Phe$^1$,pCl—D-Phe$^2$,D-3-Pal$^3$,D-Arg$^6$, |  |  |  |

The replacement of D-Trp$^3$ in the model peptide (I) by D-3-Pal$^3$ increased the antiovulatory activity, since the model peptide caused 40% AOA (antiovulatory activity) at 0.75 μg and analog II caused 58% AOA at 0.5 μg. However, at a dosage of 1 μg, analog II caused 78% AOA and the model peptide caused 83% AOA; i.e., no significant difference at 1.0 μg.

Analogs XI and XII were designed to retain D-3-Pal$^3$ of analog II, but to replace N-Ac-pCl-D-Phe$^1$ with N-Ac-D-2-Nal$^1$ and with N-Ac-3,4-diCl-D-Phe$^1$. In other words, an aromatic amino acid was retained for position 1. Analog XI caused 100% AOA at 500 ng and is the most potent of reported antagonists of LHRH to inhibit completely ovulation in the rat.

Analogs I, XI and XII were also tested by the oral route of administration for inhibition of ovulation in the rat, since the projected human application would be by

|  |  | Dose (μg) | % AOA |
|---|---|---|---|
| I. | [N—Ac—(pCl—D-Phe)$^{1,2}$,Trp$^3$D-Arg$^6$D-Ala$^{10}$]—LHRH | 0.75 | 40 |
| II. | [D-3-Pal$^3$]—LHRH | 0.50 | 58 |
| III. | [D-2-Pal$^3$]—LHRH | 1.0 | 29 |
| IV. | [D-4-Pal$^3$]—LHRH | 0.5 | 14 |
| V. | [D-3-Pal$^3$D-3-Pal$^6$]—LHRH | 1.0 | 50 |
| VI. | [D-4-Pal$^3$D-4-Pal$^6$]—LHRH | 6.0 | 63 |
| VII. | [D-Trp$^3$D-3-Pal$^6$]—LHRH | 2.0 | 13 |
| VIII. | [D-3-Pal$^3$D-Trp$^6$]—LHRH | 1.0 | 0 |
| IX. | [D-3-Pal$^3$D-Arg$^6$D-Abu$^{10}$]—LHRH | 1.0 | 10 |
| X. | [D-3-Pal$^3$D-3-Pal$^6$]—LHRH | 1.0 | 17 |

Replacement of D-Trp$^3$ in I with D-2-Pal$^3$ in III and D-4-Pal$^3$ in IV were less effective than replacement with D-3-Pal$^3$ in II on the basis of 29% AOA at 1 μg and 14% AOA at 0.5 μg, respectively.

Replacement of D-Trp$^3$ and D-Arg$^6$ in the model peptide with D-3-Pal$^{3,6}$, resulted in analog V showing 50% AOA at 1 μg. For the pair, analogs V and II, D-Arg$^6$ was better than D-3-Pal$^6$.

Replacement of D-Trp$^3$ and D-Arg$^6$ of the model peptide with D-4-Pal$^{3,6}$, resulted in analog VI showing 63% AOA at 6.0 μg.

Replacement of D-Arg$^6$ in analog IV by D-4-Pal$^6$ to give analog VI resulted in a two-fold increase in potency since analog VI caused 63% AOA and analog IV caused 33% AOA, both at 6 μg.

Retaining D-Trp$^3$ of the model peptide and replacing D-Arg$^6$ with D-3-Pal$^6$ resulted in an analog, VII, showing 13% AOA at 2 μg. Consequently, D-Arg$^6$ was superior to D-3-Pal$^6$ when D-Trp was in position 3.

Replacement of D-Trp$^3$ and D-Arg$^6$ in the model peptide with D-3-Pal$^3$ and D-Trp$^6$ to give VIII resulted in zero AOA at 1 μg.

Replacement of D-Trp$^3$ and D-Ala$^{10}$ in the model peptide with D-3-Pal$^3$ and D-Abu$^{10}$ resulted in 10% AOA at 1 μg; consequently, D-Ala$^{10}$ is superior to D-Abu$^{10}$ when comparing analogs IX and II.

Replacement of D-Trp$^3$ and D-Arg$^6$ in the model peptide with D-3-Pal$^{3,6}$ and retaining the Gly$^{10}$ of LHRH instead of having D-Ala$^{10}$ resulted in analog X showing 17% AOA at 1 μg; D-Ala$^{10}$ was superior to Gly on comparing analogs X and V.

Analogs II-X have the moieties N-Ac-(pCl-D-Phe)$^{1,2}$. Many analogs with pCl-D-Phe in position 1 are generally known to have enhanced potency, particularly when D-Arg is in position 6, over previous analogs oral administration. The data in Table 3 resulted from the administration at noon. When the administration is at 2:30 PM, effectiveness is reduced, presumably because of the LH surge. Analog I caused 100% AOA at a 2 mg dosage with administration at noon and 71% AOA/2 mg and 50% AOA/1 mg by administration at 2:30 PM Nekola et al. [Science 218, 160–162 (1982)] have reported on the oral activity of I under diverse conditions.

Analogs XI and XII, at an oral dosage at noon of 500 μg caused 56% and 63%, respectively, inhibition of ovulation. Analog XI indicated 10% AOA at 250 μg, and analog XII showed no activity at 250 μg.

By the subcutaneous route of administration, analog XI is apparently more potent than analog XII since 250 ng caused 57% AOA, but analog XII was inactive at 250 ng. However, analogs XI and XII showed essentially equivalent activities when tested orally at 500 μg; 56% and 63%, respectively.

TABLE 3

| Assays of Antagonists for Oral Activity | | | | |
|---|---|---|---|---|
| Analog | Dose* | Rats Ovu. No. Rats | No. Ova. | % AOA |
| Control | 0.2 ml H$_2$O | 9/9 | 14.9 ± 0.8 | 0 |
| I | 2 mg | 0/8 | 0 | 100 |
| XI | 500 μg | 4/9 | 6.1 ± 2.5 | 56 |
|  | 250 μg | 9/10 | 13.0 ± 1.8 | 10 |
| XII | 500 μg | 3/8 | 5.6 ± 2.7 | 63 |
|  | 250 μg | 5/5 | 12.2 ± 1.0 | 0 |

*The dosage was administered at noon.

EXAMPLES OF PYRIDYL-ALANYL PEPTIDES

The several examples of pyridyl-alanyl-peptides set forth in this document exemplify the diversity of synthetic analogs which have one or more moieties of the pyridylalanines. It is obvious that other substituents in the positions of the decapeptides which are not occupied by one or more pyridylalanines are quite possible and are within the scope of this invention.

When analog XI was administered subcutaneously to rats at three dose levels, 10 and 30 and 100 μg, 40 hrs before anticipated ovulation, there was 100% inhibition of ovulation.

These pyridylalanyl-decapeptides are useful in mammalian species to inhibit completely ovulation for control of conception, and constitute novel therapeutic agents having oral activity and a prolonged duration of activity which is useful for regulation of reproduction.

What is claimed:

1. [N-Ac-D-2-Nal$^1$,pCl-D-Phe$^2$,D-3-Pal$^3$,D-Arg$^6$,D-Ala$^{10}$]-LHRH.

2. Analogs of LHRH wherein
position 1 is N-Ac-pCl-D-Phe,
   N-Ac-D-2-Nal, or
   N-Ac-3,4-diCl-D-Phe;
position 2 is pCl-D-Phe;
position 3 is D-2-Pal,
   D-3-Pal,
   D-4-Pal, or
   D-Trp;
position 6 is D-2-Pal,
   D-3-Pal,
   D-4-Pal, or
   D-Arg,
with at least one of position 3 or 6 being D-2-Pal, D-3-Pal, or D-4-Pal; and
position 10 is D-Ala or the unsubstituted normally occuring Gly.

3. The LHRH analog of claim 2 which is [N-Ac-(pCl-D-Phe)$^{1,2}$, D-3-Pal$^3$, D-Arg$^6$, D-Ala$^{10}$]-LHRH.

4. The LHRH analog of claim 2 which is [N-Ac-(pCl-D-Phe)$^{1,2}$, D-2-Pal$^3$, D-Arg$^6$, D-Ala$^{10}$]-LHRH.

5. The LHRH analog of claim 2 which is [N-Ac-(pCl-D-Phe)$^{1,2}$, D-4-Pal$^3$, D-Arg$^6$, D-Ala$^{10}$]-LHRH.

6. The LHRH analog of claim 2 which is [N-Ac-(pCl-D-Phe)$^{1,2}$, D-Trp$^3$, D-3-Pal$^6$, D-Ala$^{10}$]-LHRH.

7. The LHRH analog of claim 2 which is [N-Ac-(pCl-D-Phe)$^{1,2}$, D-3-Pal$^{3,6}$, D-Ala$^{10}$]-LHRH.

8. The LHRH analog of claim 2 which is [N-Ac-(pCl-D-Phe)$^{1,2}$, D-4-Pal$^{3,6}$, D-Ala$^{10}$]-LHRH.

9. The LHRH analog of claim 2 which is [N-Ac-(pCl-D-Phe)$^{1,2}$, D-3-Pal$^{3,6}$]-LHRH.

10. The LHRH analog of claim 2 which is [N-Ac-3,4-diCl-D-Phe$^1$, pCl-D-Phe$^2$, D-3-Pal$^3$, D-Arg$^6$, D-Ala$^{10}$]-LHRH.

* * * * *

UNITED STATES PATENT AND TRADEMARK OFFICE
CERTIFICATE OF CORRECTION

PATENT NO. : 4,504,414

DATED : March 12, 1985

INVENTOR(S) : K. Folkers; C. Y. Bowers; T. M. Kubiak; and J. Stepinski

It is certified that error appears in the above-identified patent and that said Letters Patent is hereby corrected as shown below:

In the Examples, column 3, Table 1, No. XII., "pCl-D-Phehu" should read -- pCl-D-Phe$^2$ --.

In the Chemical Results and Biological Activities, line 6 spanning Columns 5 and 6, "XII. [N-Ac-3,4-diCL-D-Phe$^1$, pCl-D-Phe$^2$, D-3-Pal$^3$, D-Arg$^6$," should read --XII.[N-Ac-3,4-diCl-D-Phe$^1$, pCl-D-Phe$^2$, D-3-Pal$^3$, D-Arg$^6$, D-Ala$^{10}$]-LHRH 0.5 82 2/11--

Signed and Sealed this

Twentieth Day of August 1985

[SEAL]

Attest:

DONALD J. QUIGG

Attesting Officer

Acting Commissioner of Patents and Trademarks